United States Patent
Lindh, Sr. et al.

(10) Patent No.: US 8,100,941 B2
(45) Date of Patent: Jan. 24, 2012

(54) COLLAPSIBLE BARBED SUTURES HAVING REDUCED DRAG AND METHODS THEREFOR

(75) Inventors: David Lindh, Sr., Flemington, NJ (US); Jesse G. Nawrocki, Annandale, NJ (US); Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 737 days.

(21) Appl. No.: 12/140,311

(22) Filed: Jun. 17, 2008

(65) Prior Publication Data

US 2009/0312791 A1 Dec. 17, 2009

(51) Int. Cl.
*A61B 17/04* (2006.01)
*A61B 17/00* (2006.01)

(52) U.S. Cl. ........................................ 606/228; 606/213

(58) Field of Classification Search ............... 606/220, 606/223, 228, 219, 216, 151, 148, 153; 83/522.14; 128/848
See application file for complete search history.

(56) References Cited

U.S. PATENT DOCUMENTS

| | | | |
|---|---|---|---|
| 3,072,986 A | 1/1963 | Lafnaer | |
| 3,123,077 A | 3/1964 | Alcamo | |
| 3,463,436 A | 8/1969 | Foster | |
| 3,570,497 A | 3/1971 | Lemole | |
| 4,069,825 A | 1/1978 | Akiyama | |
| 4,950,285 A | 8/1990 | Wilk | |
| 5,053,047 A | 10/1991 | Yoon | |
| 5,074,874 A | 12/1991 | Yoon et al. | |
| 5,123,913 A | 6/1992 | Wilk et al. | |
| 5,425,747 A | 6/1995 | Brotz | |
| 5,500,000 A | 3/1996 | Feagin et al. | |
| 5,531,761 A | 7/1996 | Yoon | |
| 5,549,619 A | 8/1996 | Peters et al. | |
| 5,584,859 A | 12/1996 | Brotz | |
| 5,643,295 A | 7/1997 | Yoon | |
| 5,665,109 A | 9/1997 | Yoon | |
| 5,683,417 A | 11/1997 | Cooper | |
| 5,919,233 A | 7/1999 | Knopf et al. | |
| 5,931,855 A | 8/1999 | Buncke | |
| 7,021,316 B2 | 4/2006 | Leiboff | |
| 7,125,413 B2 | 10/2006 | Grigoryants et al. | |
| 7,850,894 B2 * | 12/2010 | Lindh et al. ................... | 264/320 |
| 2007/0005110 A1 | 1/2007 | Collier et al. | |
| 2007/0257395 A1 | 11/2007 | Lindh | |
| 2008/0132943 A1 * | 6/2008 | Maiorino et al. ............. | 606/228 |

FOREIGN PATENT DOCUMENTS

| | | |
|---|---|---|
| EP | 1929961 A | 6/2008 |
| WO | WO 2009097556 A2 | 8/2009 |
| WO | WO 2009129251 A2 | 10/2009 |

* cited by examiner

*Primary Examiner* — Vy Q Bui

(57) ABSTRACT

A barbed suture includes a flexible thread having a leading end and a trailing end, and a plurality of barbs projecting from the flexible thread. The flexible thread has a plurality of web-like openings formed therein, whereby each of the openings is disposed adjacent one of the barbs. The openings enhance the flexibility of the barbs and provide space for the barbs to collapse inwardly as the leading end of the flexible thread is pulled through a medium such as tissue. When the barbs are collapsed, the diameter of the barbed sections is preferably no greater than the diameter of the non-barbed sections. In one embodiment, a support element interconnects at least one of the barbs and the flexible thread for reinforcing the at least one barb and resisting flexure of the at least one barb toward the leading end of the flexible thread.

19 Claims, 8 Drawing Sheets

COLLAPSIBLE BARBED SUTURES HAVING REDUCED DRAG AND METHODS THEREFOR

BACKGROUND OF THE INVENTION

1. Field of the Invention

The present invention generally relates to surgical sutures, and more specifically relates to surgical sutures having projecting barbs used for anchoring the sutures in tissue and prosthetic devices.

2. Description of the Related Art

Surgical sutures are used for closing wounds and surgical incisions, and repairing damaged muscles, vessels, and tissue. Typically, a needle is attached to one end of the suture, and the needle is drawn through tissue to form one or more loops holding the tissue together. The suture is subsequently tied off in one or more knots so that the tissue will remain drawn together, or so that a prosthetic device will remain anchored in place.

Although sutures are very effective for closing wounds and incisions, there are a number of problems associated with conventional sutures. Many of these troubles are directly related to the knots used to secure sutures in place. If the knots are not tied properly, defects may arise including slippage, knot breakage, and re-opening of the wound or incision. In addition, using knots to secure sutures may distort tissue, restrict blood flow, increase the formation of scars, impede wound healing, and result in infection.

In response to the deficiencies associated with conventional sutures, barbed sutures have been developed. Unlike conventional sutures, barbed sutures have projecting barbs that allow the suture to be used to close wounds, approximate tissue, tighten tissue, and attach prosthetic devices without using knots. U.S. Pat. No. 5,931,885 discloses a barbed suture that is used for cosmetic procedures such as brow-lifts and face-lifts.

Referring to FIG. 1, a barbed suture 20 is generally formed by cutting a core thread 22 with a cutting blade 24. FIG. 1 illustrates an exemplary cut, whereby the cutting blade 24 first cuts into the core thread 22 at an angle β of approximately 30 degrees relative to a longitudinal axis x-x of the core thread to a depth of approximately 0.08 inches, and subsequently further cuts into the core thread for a distance of approximately 0.024 inches at an angle of approximately 0 degrees to form projecting barbs 26. After the cut is completed, the barb 26 remains connected to the core thread 22 through a base 28. During cutting, the core thread 22 is typically placed and held on a cutting vice or support in a manner well known in the art. A template may be used to guide the cutting blade 24.

Cutting barbs as shown in FIG. 1 requires the use of a mechanical shearing methodology that will rapidly dull the cutting edge of the cutting blade, thereby requiring frequent changes of the cutting blade. The cutting methodology is also negatively affected by the typical extruded diameter variation in the target thread. This variation in diameter requires a cutting head that must be frequently adjusted in fine diameter threads as small changes in thread diameter result in significantly thinner/weaker barbs, or in thicker threads resulting in thicker, stiffer barbs that will cause a variation in frictional drag during application.

The cuts in the core thread act as stress concentration points. In applications where a significant or pulsatile load is placed on the barbed suture, i.e., heart valve repair or replacement procedures and orthopedic applications, a given barb may fail, or begin peeling away from the core thread. Once this occurs, due to the fibrous nature of the suture material, the barb may be stripped off the core thread along a significant length of the suture causing catastrophic failure of the suture.

For example, referring to FIG. 2, after the cutting steps described above, the cut barbs 24 remain flexibly coupled with the core thread 22 via the bases 28. When a leading end 30 of the barbed suture 20 is pulled in the direction D1, the barbs 24 collapse inwardly toward the core thread 22, and deflect toward a trailing end 32 of the barbed suture 20. When the trailing end 32 of the barbed suture is pulled in the direction $D_2$, trailing edges 34 of the barbs 26 push against the surrounding media so as to deflect the barbs outwardly and away from the core thread 22. As the barbed suture is pulled in the direction $D_2$, great stress builds upon the previously cut base sections 28. As a result, one or more of the barbs 26 may fail at the base sections 28 and delaminate from the core thread 22. This type of structural failure may result in catastrophic failure of the barbed suture, and may also result in serious injury to, or the death of, a patient.

In order to improve the reliability and durability of barbed sutures, some have attempted to enhance the strength of the connection between the barbs and the core thread. Unfortunately, these efforts have provided barbed sutures having rigid or relatively inflexible barbs provided along the barb shaft. The rigid barbs remain inflexible when pulled through tissue, impart significant drag, and damage tissue during passage. The drag and tissue damage effects become exaggerated when the barbed elements oppose each other along the barb shaft resulting in sawing of the tissue during motion. Due to this "sawing effect", the tissue may be damaged.

In some instances, braided barbed sutures having more durable barbs are used. In one embodiment of commonly assigned U.S. Patent Application Publication No. 2007/0005110, the disclosure of which is hereby incorporated by reference herein, a prosthetic heart valve has a valve sewing ring and braided barbed sutures are disposed in the valve sewing ring by first passing the sutures through an annulus and then passing the sutures through the valve sewing ring. Approximately 12-20 sets of braided barbed sutures are passed through the valve sewing ring to secure the prosthetic heart valve in place. The heart valve is then parachuted down the sets of barbed sutures and seated in place within the annulus. After the heart valve has been parachuted down into place, the barbs prevent the valve from being moved in the opposite, upward direction for holding the heart valve in place without requiring knots.

In spite of the above advances, there remains a need for barbed sutures having improved reliability, durability and efficacy. In addition, there remains a need for barbed sutures that are easier to manufacture and deploy. There also remains a need for barbed sutures that cause little or no damage to tissue as the suture is passed through the tissue while retaining their structural integrity.

SUMMARY OF THE INVENTION

In one embodiment, a barbed suture includes a flexible thread having a leading end, and a trailing end, and a plurality of barbs projecting from the flexible thread. When not under strain or stress, the barbs normally project toward the trailing end of the flexible thread. The flexible thread desirably has a plurality of openings formed therein, whereby at least one of the openings formed in the flexible thread is disposed adjacent one of the barbs. In one embodiment, the plurality of openings formed in the flexible thread extend through the flexible thread for defining a web-like structure extending along the length of the flexible thread. The plurality of openings preferably enhance the flexibility of the barbs and provide space for the barbs to collapse inwardly toward the flexible thread as the leading end of the flexible thread is pulled through a medium, such as tissue or a valve sewing ring.

In one embodiment, a barbed suture includes a web support element extending between at least one of the barbs and the flexible thread for reinforcing the at least one barb and resisting flexure of the at least one barb toward the leading end of said flexible thread. In one embodiment, a plurality of web support elements extend between the barbs and the flexible thread for reinforcing the barbs. In a highly preferred embodiment, the web support elements interconnect the barbs and the core thread. The web support elements desirably resist flexure of the barb toward the leading end of the suture when the suture is pulled in the removal or rearward direction. The web support elements preferably reinforce the barbs, thereby reducing the need for large barb bases typically required to resist the cantilever loading. The web support elements also greatly increase the strength of the attachment of the barbs to the thread, and greatly minimize the likelihood of the barbs delaminating from the thread when the suture is pulled in the removal direction. As a result, the barb bases may be made smaller than would be possible if web support elements were not provided.

In one embodiment, the barbed suture is extruded. The barbed suture preferably comprises a biocompatible material such as a biocompatible polymer. The barbs and the openings in the thread may be formed using a punching operation.

In one embodiment, a section of the flexible thread is looped, and at least one of the barbs in the looped section is passed through one of the openings in the flexible thread. The looped section may be at the leading end or the trailing end of the barbed suture for securing the ends of the barbed suture without tying knots. In one embodiment, the looped section of the flexible thread is adjacent the leading end of the flexible thread and the opening through which the looped section passes is also located adjacent the leading end of the thread. By looping one or more barbs through one of the openings, an end of a barbed suture may be secured without tying a knot. In one embodiment, the looped section may be located anywhere along the length of the barbed suture.

In one embodiment, a barbed suture includes a flexible thread having an outer surface and a plurality of recesses is formed in the outer surface. As the leading end of the flexible thread is passed through a medium (e.g. tissue), the barbs are adapted to collapse inwardly toward the thread and be seated in the recesses for minimizing the outer diameter of the barbed suture.

In one embodiment, each of the barbs is connected to the flexible thread by a base section, and the base section of at least one of the barbs has a crease formed therein for enhancing the flexibility of the barbs. In a highly preferred embodiment, each of the barbs has a crease formed therein for enhancing the flexibility of the barbs so as to minimize drag and/or the "sawing" effect as the barbed suture is pulled through a medium such as tissue. In one embodiment, the flexible thread has a longitudinal axis that extends between the leading and trailing ends thereof and the creases extend in planes that are substantially parallel with the longitudinal axis.

In one embodiment, a barbed suture includes a flexible thread having a leading end, and a trailing end, and a plurality of barbs projecting from the flexible thread and extending toward the trailing end of the flexible thread, whereby each barb includes a base connected with the flexible thread and a tip remote from the base. The flexible thread preferably has a plurality of openings extending therethrough, whereby each of the openings is disposed adjacent the base of one of the barbs. The openings enhance the flexibility of the barbs, particularly at the bases of the barbs, thereby minimizing drag as the barbed suture is passed through a medium (e.g. tissue). The openings also minimize the likelihood of the "sawing effect" discussed above. In addition, the openings are preferably adapted to provide space for the barbs when the barbs collapse inwardly toward the flexible thread for minimizing the diameter of the barbed suture.

In one embodiment, a flexing element for preflexing the barbs toward the trailing end of a flexible thread includes a leading face, a trailing face, and a barb flexing opening extending between the leading and trailing faces thereof. The barb flexing opening has a smaller diameter than the diameter of the barbed suture when the barbs are fully extended. The barb flexing opening of the flexing element is adapted to force the barbs inwardly toward the flexible thread as the leading end of the flexible thread is pulled through the barb flexing opening. In one embodiment, the barb flexing opening tapers inwardly between the leading and trailing faces of the barb flexing element.

In one embodiment, a barbed suture includes a flexible thread having a plurality of web-like openings extending therethrough, whereby the plurality of openings extend between a leading end and a trailing end of the flexible thread. The barbed suture includes a plurality of barbs projecting outwardly from the flexible thread, each barb including a base connected with the flexible thread, with each base being in substantial alignment with at least one of the web-like openings. The web-like openings desirably provide space for the barbs when the barbs are collapsed inwardly toward the flexible thread for minimizing the diameter of the barbed suture. The openings also enhance the flexibility of the bases of the barbs to minimize drag and the "sawing effect" described herein. The outer surface of the flexible thread may include recesses for seating the barbs when the barbs are collapsed inwardly, further minimizing the drag and the "sawing effect". In one embodiment, a section of the flexible thread is looped over upon itself and at least one of the barbs in the looped section extends through one of the web-like openings for securing an end of the barbed suture without tying a knot.

The present invention provides barbed sutures having base fiber or thread diameters that are preferably equal to or greater than the diameter of the collapsed barbed elements. This may be achieved using unique geometric structures that minimize the barb profile.

In one embodiment, the rigidity of the barbs on a barbed suture is minimized by pre-flexing the barbs prior to use. The preflexing of the barbs provides for easier passage of the barbed suture through tissue and minimal "sawing effect" with no loss of core fiber strength.

In one embodiment, the outer surface of the core fiber is provided with recesses that are adapted to receive the barbs when the barbs are collapsed inwardly. The recesses enable the barbs in the collapsed position to have a diameter that is no greater than the outer diameter of the core section. In one embodiment, the flexible core thread includes a plurality of web-like openings that are aligned with the bases of the barbs. The web-like openings enhance the flexibility of the barbs and provide space for the barbs to collapse inwardly so as to minimize the outer diameter of the barbs when the barbs are in the collapsed configuration. In one embodiment, the projecting barbs may be provided on only one side of the core element.

In one embodiment, the barbed suture may be looped and an end pulled through any one of the openings formed in the core section to provide further fixation or to anchor the ends of the device at the beginning and/or end of a wound where knots would be tied using traditional sutures.

The barbs may be arranged on the core thread according to any desired configuration, and may be formed using any suitable method including those well known in the art. These methods may include injection molding, stamping, punching, cutting by knife or laser, etching, press forming or the like.

These and other preferred embodiments of the present invention will be described in more detail below.

DETAILED DESCRIPTION

Figure 1:
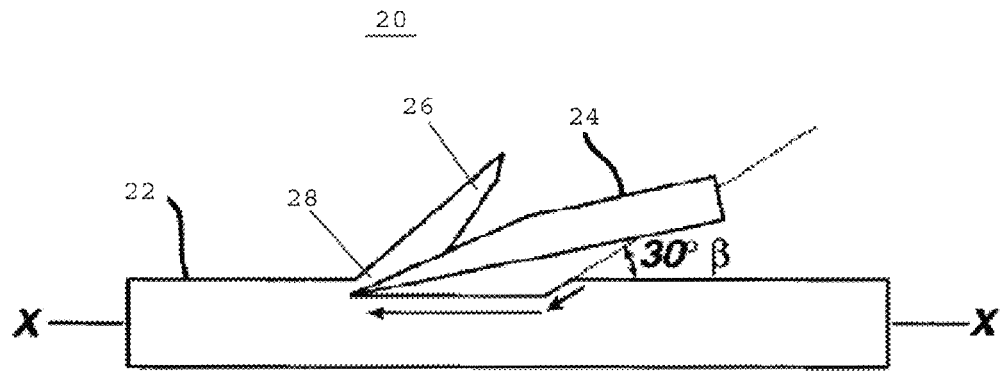
FIG. 1 shows a prior art method of making a barbed suture.
Figure 2:
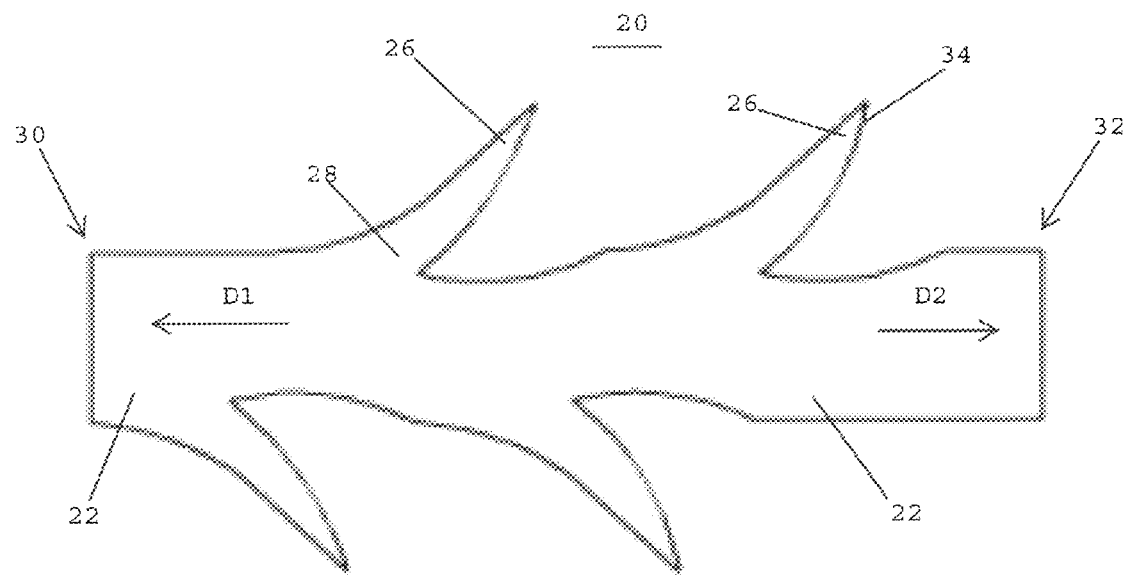
FIG. 2 shows another view of the prior art barbed suture of FIG. 1.

Conventional barbed sutures tend to be rigid and relatively inflexible. Prior art attempts to improve the flexibility of barbs has often resulted in barbed sutures having barbs that easily delaminate from a core thread of the suture or barbs that exhibit inadequate load bearing properties due to increased barb flexibility. Other attempts to prevent delamination have produced rigid barbs that do not flex/collapse easily when pulled through media, which can impart significant drag and "sawing effect" media damage during passage. In addition, the drag and media damage effects become exaggerated when the barbed elements radially oppose each other along the length of the suture.

Although the present invention is not limited by any particular theory of operation, it is believed that the barbed suture disclosure herein may be pulled through tissue with minimal "sawing effect" and with no loss of core thread or fiber strength due to providing a barbed suture having pre-flexed barbs for minimizing the rigidity of the barbs when the suture is passed through tissue. In addition, the present invention provides barbed sutures having recesses formed in the outer surface of the core thread for providing a seating area for the barbs as the barbs pass through tissue so that the diameter of the barbed sections (when the barbs are collapsed) is no greater than the diameter of the non-barbed sections. In addition, the present invention provides a barbed suture having web-like openings provided in the core thread for enhancing the flexibility of the barbs so as to enable the barbs to more easily collapse inwardly when being pulled through tissue. The openings also provide space for the inwardly collapsing barbs so that the outer diameter of the collapsed barb section is no greater than the outer diameter of the non-barbed sections.

In one embodiment, the non-barbed section of the flexible thread directly preceding any barbed section has a cross-sectional diameter that is the same size or greater than the cross-sectional diameter of the barbed section when the barbs are collapsed. As a result, the diameter of the preceding non-barbed section serves to dilate the tissue prior to the barbs passing through, thereby minimizing the tissue sawing effect. In one embodiment, the material located at the base of the barb is removed to provide a plurality of openings extending along the core of the suture. In one embodiment, the material is removed by being punched out. The removal of the material to form the openings enhances the flexibility of the bases of the barbs, thereby minimizing the force required to deform the barbs. The openings in the thread also provide space for the barbs to collapse inwardly to further minimize the cross-sectional diameter of the barbed section of the suture. In one embodiment, the barbed suture may be passed through a flexing element to deform the barbs prior to passing the barbs through tissue. In one embodiment, creases may be formed in the bases of the barbs to ensure consistent and proper flexing of the barbed elements and to reduce the load necessary to ensure motion through the tissue in the direction of insertion. The creases formed in the barbs may extend in directions that are parallel to one another and parallel to a longitudinal axis of the barbed suture.

Figure 3A:
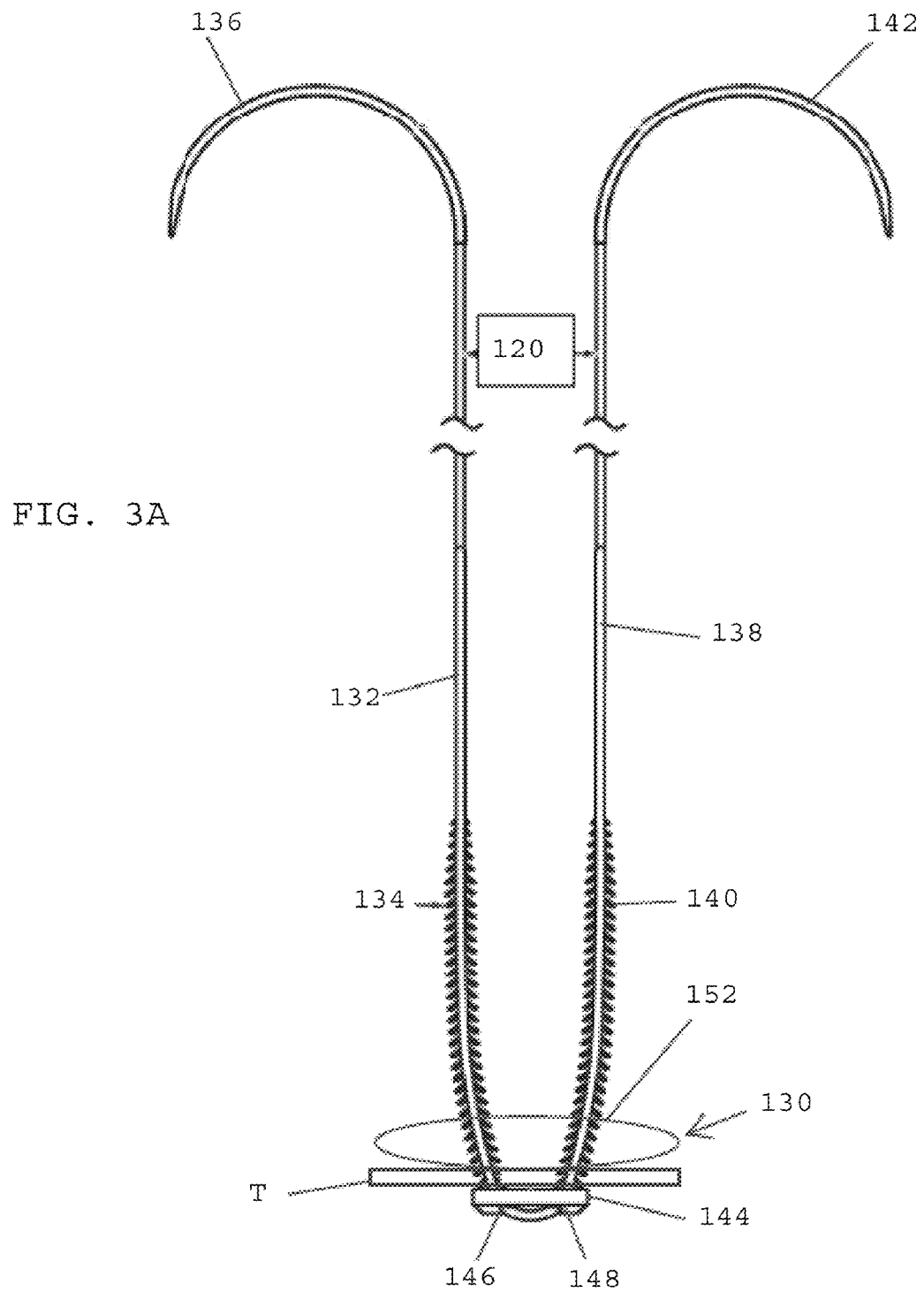
FIGS. 3A-3C show a method of securing a prosthetic device in place using a barbed suture, in accordance with one embodiment of the present invention.
Figure 3B:
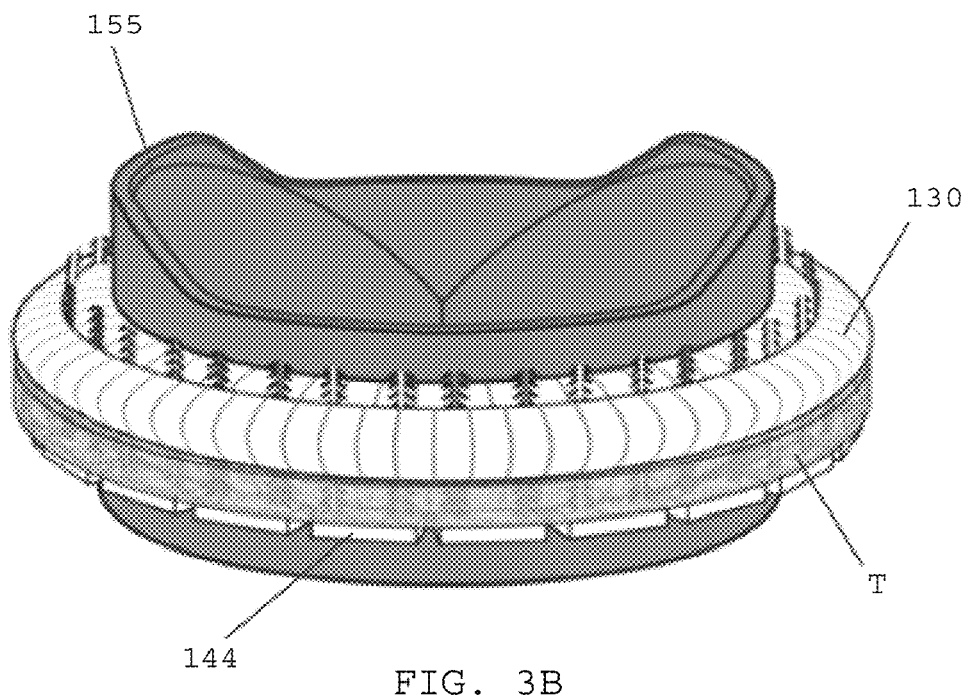
Figure 3C:
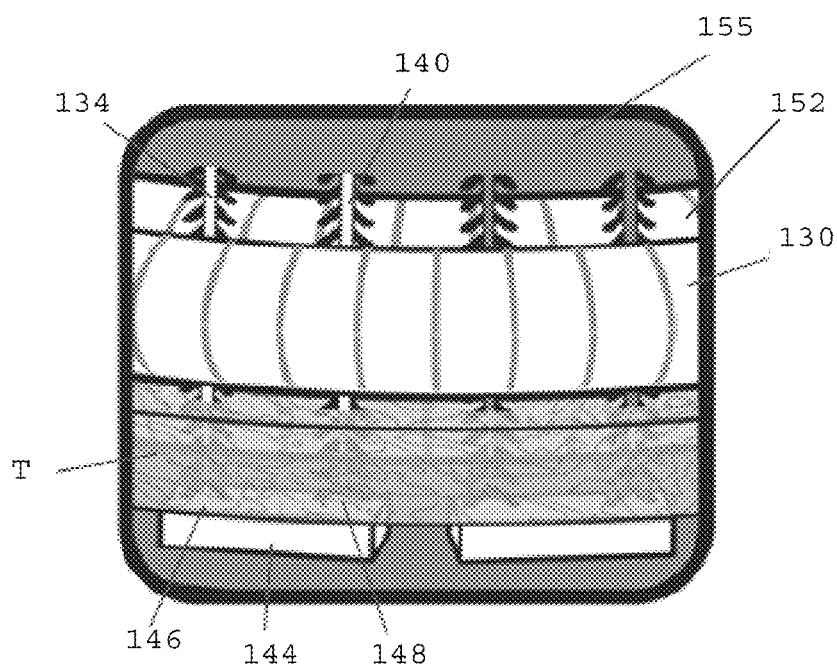

Referring to FIGS. 3A-3C, in one embodiment, a bidirectional barbed suture 120 includes a first section 132 having a first set of barbs 134 and a first suture needle 136, and a second section 138 having a second set of barbs 140 and a second suture needle 142. The first set of barbs 134 extend in a different direction than the second set of barbs 140. The bidirectional barbed suture includes a pledget 144 having first and second openings 146, 148. In one embodiment, the first suture needle 136 is passed through the first opening 146 of the pledget 144 and the second suture needle 142 is passed through the second opening 148 of the pledget 144. The pledget 144 is preferably positioned between the first set of barbs 134 and the second set of barbs 140. In one embodiment, the pledget 144 may be centered between the first and second sets of barbs 134, 140. Although a bidirectional barbed suture 120 is shown in FIG. 3A, in other preferred embodiments, a unidirectional barbed suture may be used.

Referring to FIGS. 3A-3C, in one embodiment, the barbed suture is used to secure a prosthetic heart valve having a valve sewing ring 130, whereby the barbed suture is passed through tissue T and the valve sewing ring 130. The first suture needle 136 is pulled through the tissue T and the valve sewing ring 130 so that some of the first barbs 134 extend from the top surface 152 of the valve sewing ring 130. The second suture needle 142 is also pulled through the tissue T and the valve sewing ring 130 so that some of the second barbs 140 extend from the top surface 152 of the valve sewing ring 130. Referring to FIG. 3B, a plurality of barbed sutures may be used and the above described steps may be repeated around the perimeter of the valve sewing ring 130 for effectively securing the heart valve 155 to the tissue T. Referring to FIG. 3C, in one embodiment, the first and second barbed sections 134, 140 of each bidirectional barbed suture preferably extend along axes that are substantially parallel with one another. In one embodiment, the spacing between the first and second barbed sections 134, 140 of the suture corresponds to the spacing between the openings 146, 148 in the pledget 144. In one embodiment, the spacing between the first and second barbed sections 134, 140 of the suture generally matches the spacing between the openings 146, 148 of the pledget 144.

Figure 4:
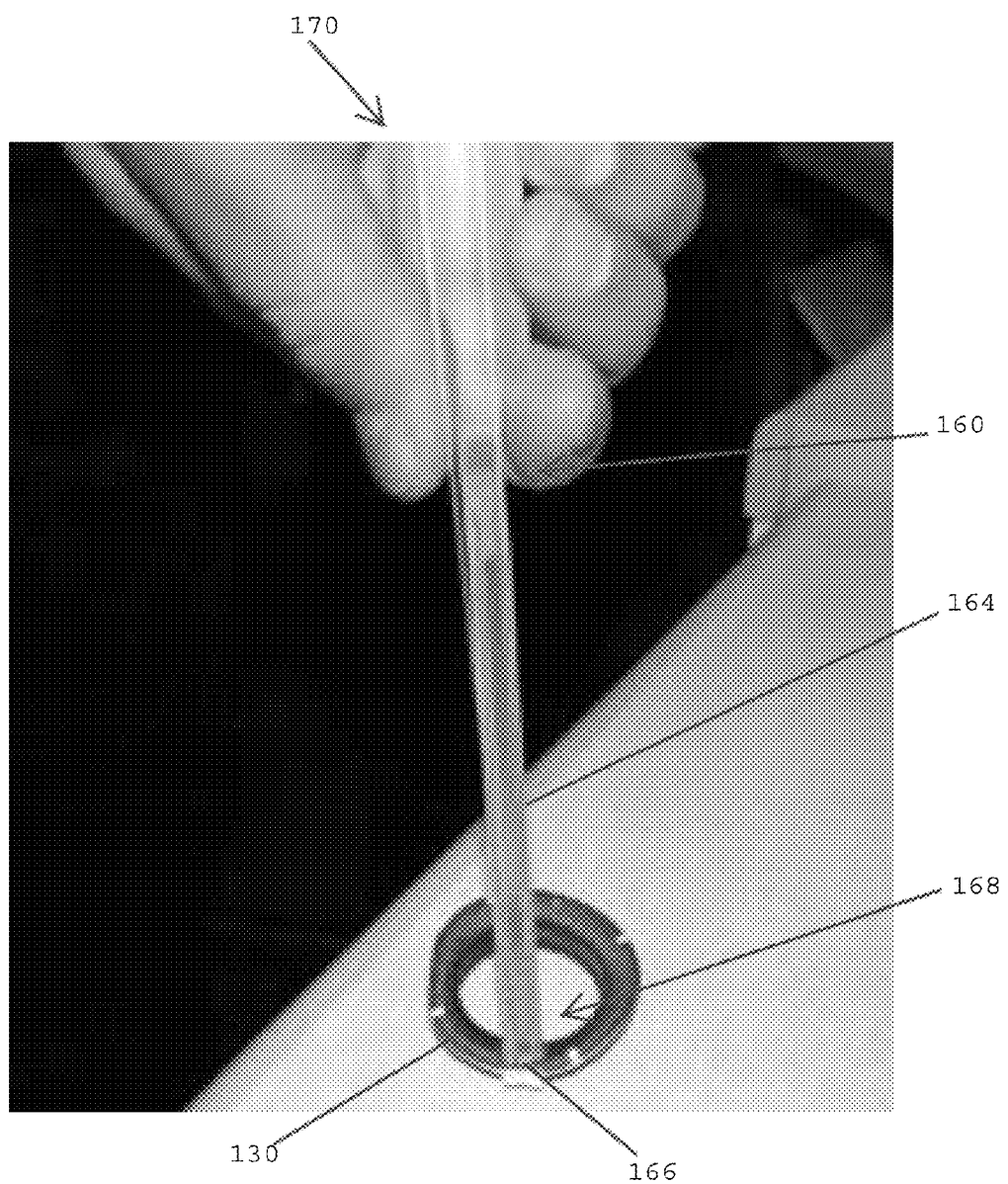
FIGS. 4 and 5 show a method of tensioning the barbed suture of FIGS. 3A-3C, in accordance with one embodiment of the present invention.
Figure 5:
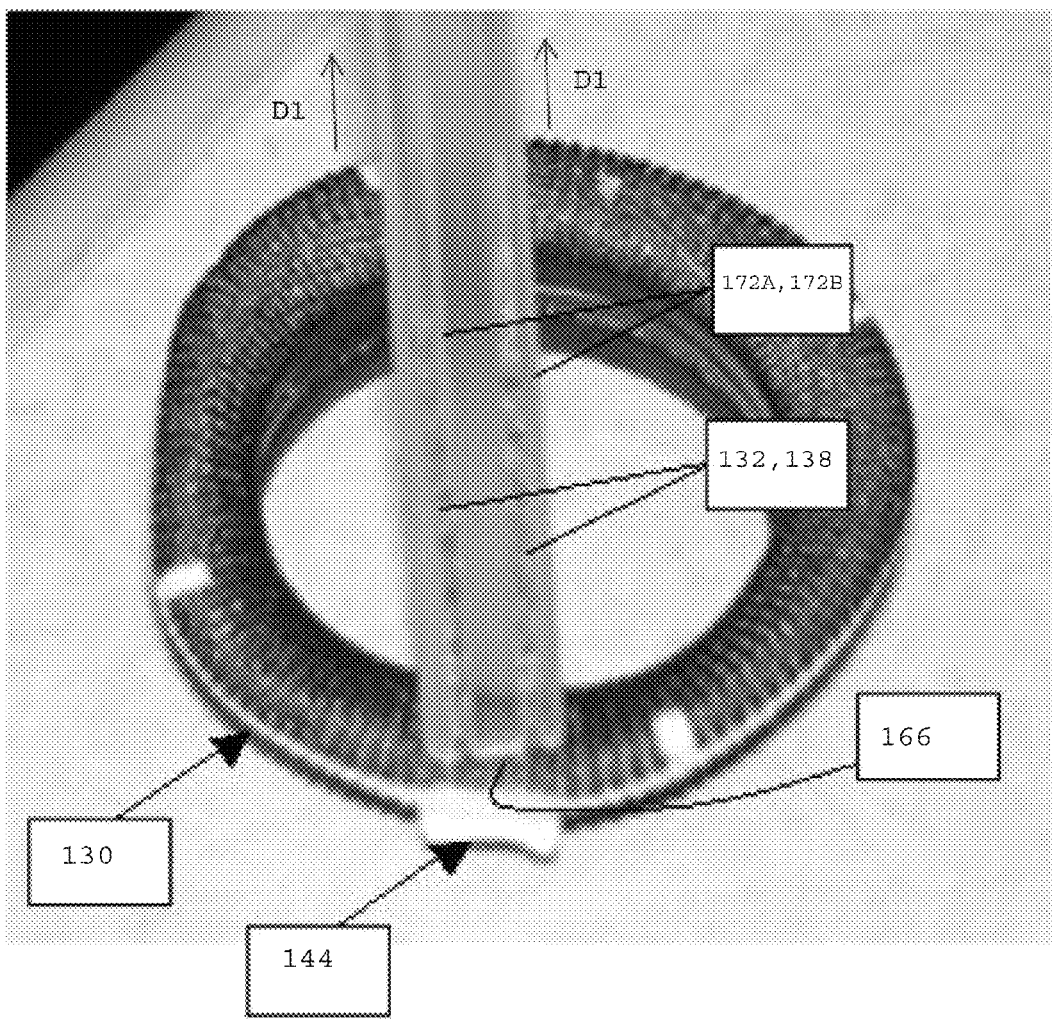

Referring to FIG. 4, in one embodiment, a tensioning device 160 is used for applying tension to the barbed sutures passed through the tissue and the valve sewing ring 130. The tensioning device may include one or more of the features disclosed in commonly assigned U.S. patent application Ser. No. 12/135,176, filed Jun. 7, 2008, the disclosure of which is hereby incorporated by reference herein. The tensioning device 160 preferably includes a shaft 164 having a pressure applying surface 166 at a distal end 168 thereof. The shaft 164 also has a proximal end 170 that may include a handle. Referring to FIG. 5, in one embodiment, the first and second sections 132, 138 of the bidirectional barbed suture are preferably disposed within respective first and second grooves 172A, 172B of the shaft 164. As the first and second sections 132, 138 are pulled toward the proximal end 170 of the shaft 164, in the direction designated $D_1$, the pressure applying surface 166 is pressed against the top surface of the valve sewing ring 130. These steps are then preferably repeated around the perimeter of the valve sewing ring 130 (see FIG. 3B) to apply tension to all of the barbed sutures. Although the present invention is not limited by any particular theory of operation, it is believed that the tensioning device shown and described in the '176 application provides highly localized pressure on tissue or valve sewing rings where needed for tensioning barbed sutures. Thus, stretching of the tissue is reduced or eliminated and improved anchoring of the sutures, tissue and/or prosthetic devices will occur.

For purposes of clarity, FIGS. 4 and 5 do not show the tissue T shown in FIGS. 3A-3C. Those skilled in the art will understand that tissue will frequently be positioned between the pledget 144 and an underside of the valve sewing ring 130. In addition, for purposes of clarity, FIGS. 4 and 5 show only the valve sewing ring 130 and do not show the heart valve portion of a prosthetic device. In one preferred embodiment, the valve sewing ring 130 shown in FIGS. 4 and 5 surrounds a heart valve (see FIG. 3B), and is preferably secured to an outer perimeter of the heart valve.

Figure 6A:
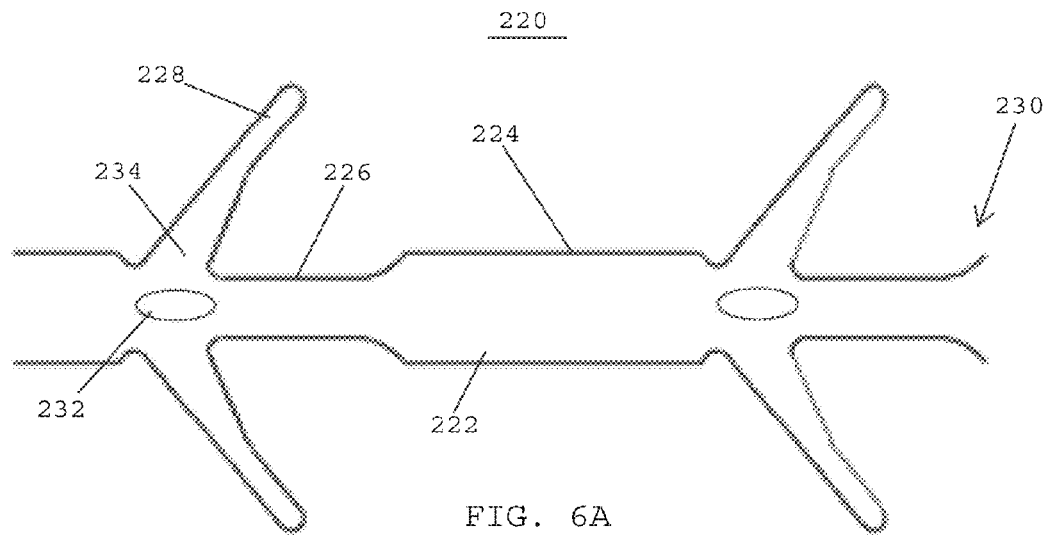
FIG. 6A shows a barbed suture, in accordance with one embodiment of the present invention.

Referring to FIG. 6A, in one embodiment, a collapsible barbed suture 220 includes a flexible thread 222 that defines the core of the suture. The flexible thread has an outer surface 224 that defines the largest diameter section of the thread 222. The barbed suture 220 includes recesses 226 formed in the outer surface 224 of the flexible thread 222. The recesses 226 are adapted to seat barbs 228 when the barbs 228 are collapsed inwardly toward the thread 222 and/or are deflected rearwardly toward the trailing end 230 of the barbed suture 220. The barbed suture 220 preferably has a web-like structure including openings 232 disposed adjacent bases 234 of opposing barbs 228. In one embodiment, the openings 232 are formed in the flexible thread 222. In one embodiment, the openings 232 extend through the flexible thread 222.

The web-like openings 232 may be formed by a wide variety of techniques well-known to those skilled in the art such as punching, cutting, etching, laser ablation, etc. Although the present invention is not limited by any particular theory of operation, it is believed that the openings 232 enhance the flexibility of the bases 234 and, in turn, the barbs 228 associated with the respective bases. It is also believed that the openings 232 provide space that enables the opposing barbs 228 to collapse inwardly, which minimizes the cross-sectional diameter of the barbed sections of the suture 220 when the barbs are collapsed. As a result, the drag generated by the barbs 228 as the suture 220 is pulled through a medium such as tissue is minimized. In addition, the recesses 226 formed in the outer surface 224 provide spaces into which the barbs 228 may collapse, which further minimizes the cross-sectional diameter of the barbed sections of the suture when the barbs are in a collapsed configuration, thereby minimizing the "sawing" effect that damages tissue.

Figure 6B:
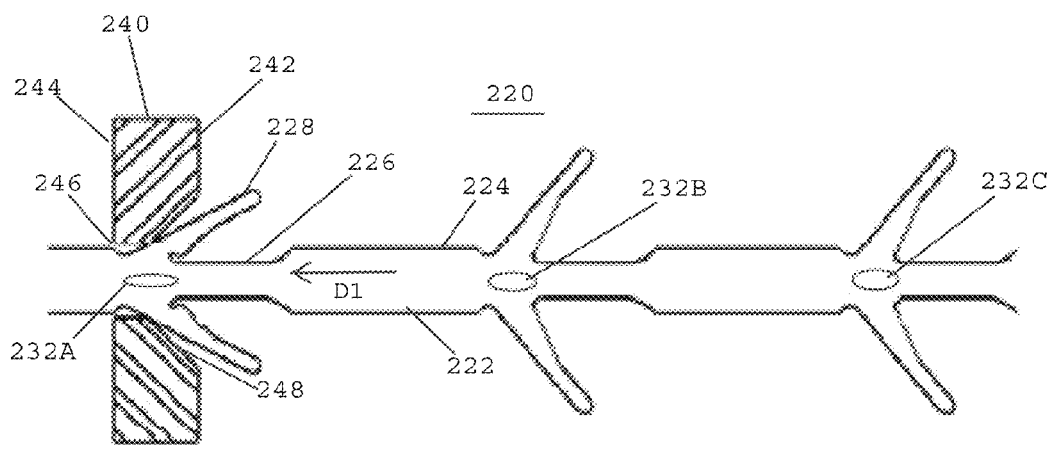
FIG. 6B shows the barbed suture of FIG. 6A during a preflexing step, in accordance with one embodiment of the present invention.

Referring FIG. 6B, the barbs 228 may be pre-flexed by passing the barbed suture 220 through a flexing ring or die 240. In one embodiment, the flexing ring 240 includes a first face 242, a second face 244, and an opening 246 extending between the first and second faces 242, 244. The shape of the opening 246 at the first face 242 may include tapered walls 248. In order to pre-flex the barbs 228 so as to produce a partial plastic deformation of the barbed element, to provide a preferred region for buckling of the barb and/or to minimize any rigidity or stiffness in the barbs, a leading end 250 of the barbed suture 220 is passed through the tapered opening 246 and pulled in the direction indicated by arrow $D_1$. As the barbed suture 220 is pulled through the flexing ring 240 in direction $D_1$, the barbs 228 engage the tapered opening 248 and collapse inwardly toward the recesses 226 formed in the outer surface 224 of the flexible thread 222. As noted above, the openings 232 in the thread 222 provide space for the barbs 228 to flex inwardly so that when the barbed suture is in the collapsed configuration the outer diameter of the barbed suture is no greater than the outer diameter defined by the outer surface 224 of the thread 222. As the barbs associated with the first opening 232A pass through the barb flexing opening 246, the first opening 232A is at least partially collapsed to allow the barbs to collapse inwardly. At the same time, the second opening 232B and the third opening 232C remain in their un-collapsed configurations. Although not shown in FIG. 6B, those skilled in the art will recognize that the second and third openings 232B, 232C will also collapse in sequence as the barbs associated with those openings pass through the barb flexing opening 246. In one embodiment, the flexing ring and/or the barbed suture may be heated to aid in preflexing the barbs, and to improve the collapsibility of the barbed elements during deformation.

Figure 6C:
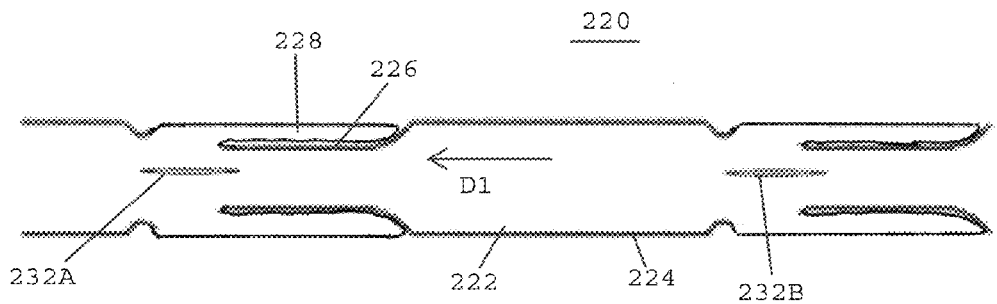
FIG. 6C shows the barbed suture of FIG. 6B with the barbs in a collapsed configuration, in accordance with one embodiment of the present invention.

FIG. 6C shows the barbed suture 220 with the barbs 228 in the collapsed configuration. The collapsed barbs 228 are seated within the recesses 226. Moreover, as the barbs 228 are collapsed, the openings 232A, 232B formed in the thread 222 are collapsed to provide additional space for the collapsing barbs 228 so that the outer diameter of the barbed section is no greater than the outer diameter of the non-barbed section of the thread 222.

Figure 7:
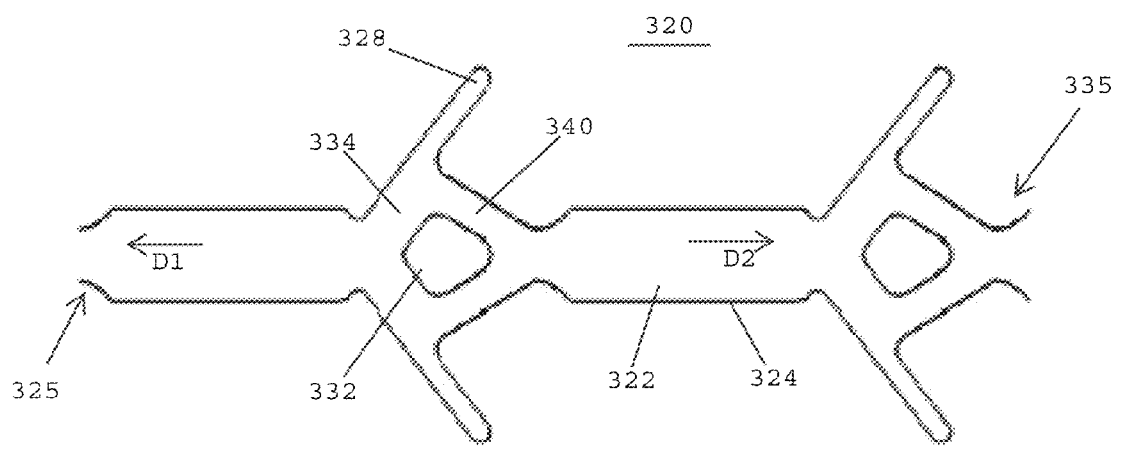
FIG. 7 shows a barbed suture, in accordance with one embodiment of the present invention.

Referring to FIG. 7, in one embodiment, a collapsible barbed suture 320 includes a flexible thread 322 that extends from a leading end 325 to a trailing end 335 thereof. The thread 322 has an outer surface 324 that defines the outer diameter of the thread. The barbed suture 320 includes a plurality of flexible, deflectable barbs 328 that project outwardly from the thread 322 at angles relative to the longitudinal axis of the barbed suture. The barbed suture includes a series of web-like openings 332 provided adjacent the bases 334 of the barbs 328. As the barbed suture 320 is pulled in the direction $D_1$, the barbs 328 collapse inwardly toward the core thread 322. The openings 332 in the thread 322 enhance the flexibility of the barbs 328 and also provide space for the barbs to collapse inwardly so that the barbs 328 in the collapsed configuration have a diameter that is preferably as small as possible, and more preferably no greater than the diameter defined by the outer wall 324 or non-barbed section of the thread 322.

In one embodiment, each barb 328 includes a web support element 340 that extends between the barb 328 and the core thread 322. In a highly preferred embodiment, the web support element 340 interconnects the barbs and the core thread 322. The web support element 340 desirably resists flexure of the barb toward the leading end 325 of the suture 320 when the suture is pulled in the direction $D_2$ (i.e. the direction of removal). The web support element 340 preferably reinforces the barb 328, thereby reducing the need for a large barb base 334 typically required to resist the cantilever loading. The web support element 340 also greatly increases the strength of the attachment of the barbs 328 to the thread 322, and greatly minimizes the likelihood of the barb 328 delaminating from the thread 322 when the suture 320 is pulled in the removal direction $D_2$. As a result, the barb base 334 may be made smaller than would be possible if the web support element 340 were not provided.

Figure 8:
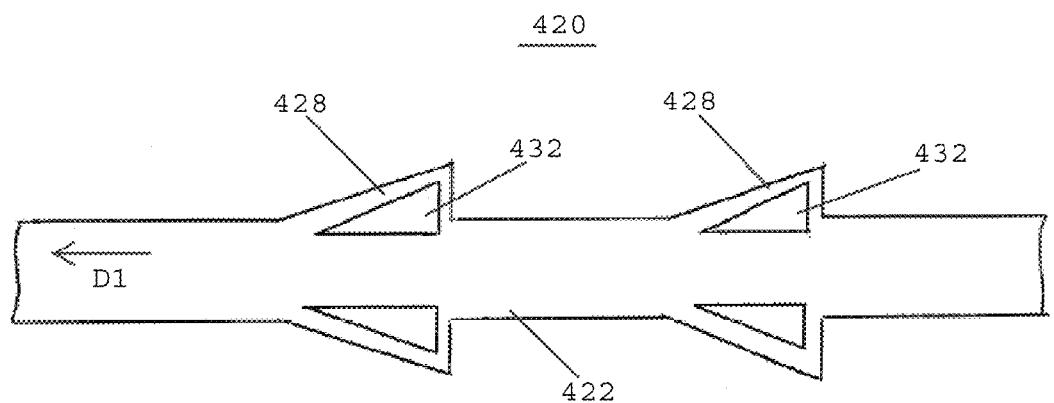
FIG. 8 shows a barbed suture in accordance with one embodiment of the present invention.

Referring to FIG. 8, in one embodiment, a collapsible barbed suture 420 includes a core thread 422 and a plurality of flexible, collapsible barbs 428 projecting outwardly from the thread 422. The barbed suture 420 includes openings 432 formed in the barbs 428. The openings 432 minimize the rigidity and stiffness of the barbs 428, thereby enabling the barbs 428 to collapse inwardly as the barbed suture is pulled in the direction indicated $D_1$. The openings 432 may also extend inwardly beyond the outer surface 424 of the thread 422.

Figure 9:
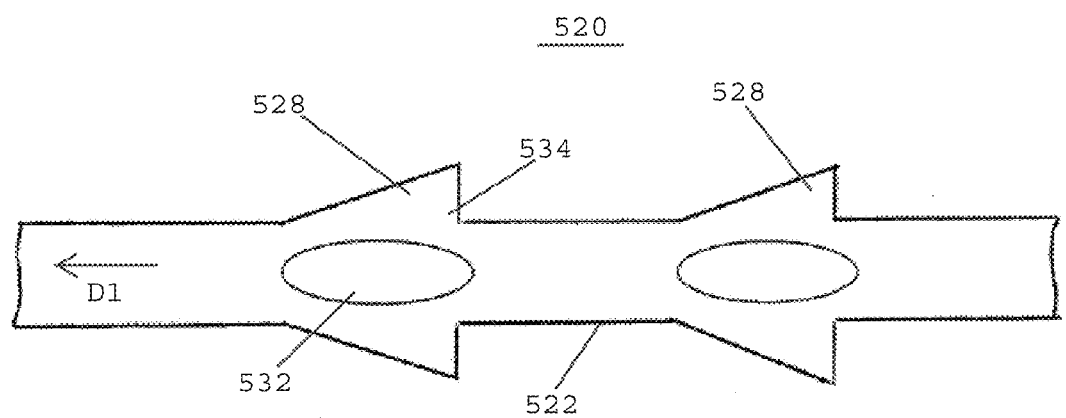
FIG. 9 shows a barbed suture, in accordance with one embodiment of the present invention.

Referring to FIG. 9, in one embodiment, a collapsible barbed suture 520 includes a flexible core thread 522 and a plurality of flexible, collapsible barbs 528 projecting outwardly from the thread 522. The barbed suture 520 has a web-like structure including openings 532 formed in the thread 522. The openings 532 are desirably located adjacent the bases 534 of the barbs 528. The openings 532 enhance the flexibility of the barbs 528 and provide space for the barbs to collapse inwardly as the barbed suture 520 is pulled through a medium such as tissue in the direction indicated $D_1$. Due to the above-described structure, when the barbs are in the collapsed configuration, the cross-sectional diameters of the barbed sections are preferably no greater than the cross-sectional diameters of the non-barbed sections.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A barbed suture comprising:
a flexible thread having a leading end, and a trailing end;
a plurality of barbs projecting from said flexible thread, wherein each said barb is connected to said flexible thread by a base section, and wherein opposing base sections on opposite sides of said flexible thread are in alignment with one another;
said flexible thread having a plurality of openings formed therein, wherein each of the openings formed in said flexible thread is disposed between and in alignment with said opposing base sections of said barbs.

2. The barbed suture as claimed in claim 1, wherein the plurality of openings formed in said flexible thread extend through said flexible thread for defining a web-like structure extending along said flexible thread.

3. The barbed suture as claimed in claim 1, wherein the plurality of openings provide space for said barbs to collapse inwardly toward said flexible thread as the leading end of said flexible thread is pulled through a medium.

4. The barbed suture as claimed in claim 3, wherein said flexible thread has an outer surface and a plurality of recesses are formed in the outer surface, and wherein pairs of recesses on opposite sides of said flexible thread are in alignment with one another.

5. The barbed suture as claimed in claim 4, wherein opposing ones of said barbs are adapted to be seated in said aligned recesses when said barbs collapse inwardly as the leading end of said flexible thread is pulled through the medium.

6. The barbed suture as claimed in claim 1, further comprising a support element extending between at least one of said barbs and said flexible thread for reinforcing said at least one barb and resisting flexure of said at least one barb toward the leading end of said flexible thread.

7. The barbed suture as claimed in claim 6, wherein said support element interconnects said at least one barb with said flexible thread, and wherein said support element defines an edge of one of said openings in said flexible thread.

8. The barbed suture as claimed in claim 1, wherein said base section of at least one of said barbs has a crease formed therein for enhancing the flexibility of said barbs.

9. The barbed suture as claimed in claim 1, further comprising a flexing element for pre-flexing said barbs toward the trailing end of said flexible thread including a leading face, a trailing face, and a barb flexing opening extending between the leading and trailing faces thereof, wherein the barb flexing opening has a smaller diameter than the diameter of said barbed suture when said barbs are fully extended, and wherein the barb flexing opening is adapted to force said barbs inwardly toward said flexible thread as the leading end of said flexible thread is pulled through the barb flexing opening.

10. A barbed suture comprising:
a flexible thread having a leading end, and a trailing end;
a plurality of barbs projecting from said flexible thread and extending toward the trailing end of said flexible thread, wherein each said barb includes a base connected with said flexible thread and a tip remote from said base;
said flexible thread having a plurality of openings extending therethrough, wherein each of the openings is disposed adjacent said base of one of said barbs; and
a flexing element for pre-flexing said barbs toward the trailing end of said flexible thread including a leading face, a trailing face, and a barb flexing opening extending between the leading and trailing faces thereof, wherein the barb flexing opening has a smaller diameter than the diameter of said barbed suture when said barbs are fully extended, and wherein the barb flexing opening is adapted to force said barbs inwardly toward said flexible thread as the leading end of said flexible thread is pulled through the barb flexing opening.

11. The barbed suture as claimed in claim 10, wherein said barbed suture is extruded.

12. The barbed suture as claimed in claim 11, wherein said barbed suture comprises a polymer.

13. The barbed suture as claimed in claim 10, wherein said openings are adapted to provide space for said barbs when said barbs collapse inwardly toward said flexible thread for minimizing the diameter of said barbed suture.

14. The barbed suture as claimed in claim 10, further comprising support elements extending between each said barb and said flexible thread for reinforcing said barbs and resisting flexure of said barbs toward the leading end of said flexible thread.

15. The barbed suture as claimed in claim 10, wherein the barb flexing opening tapers inwardly between the leading and trailing faces of said barb flexing element.

16. A barbed suture comprising:
a flexible thread having a plurality of web-like openings extending therethrough, wherein the plurality of openings extend between a leading end and a trailing end of said flexible thread;

a plurality of barbs projecting outwardly from said flexible thread, wherein opposing barbs projecting from opposite sides of said flexible thread are in alignment with one another, each said barb including a base connected with said flexible thread, wherein each one of said web-like openings is disposed between and in alignment with said opposing bases of said aligned, opposing barbs.

17. The barbed suture as claimed in claim 16, wherein said web-like openings provide space for said barbs when said barbs are collapsed inwardly toward said flexible thread for minimizing the diameter of said barbed suture.

18. The barbed suture as claimed in claim 16, wherein an outer surface of said flexible thread includes recesses for seating said barbs when said barbs are collapsed inwardly, wherein said recesses are in alignment with one another.

19. The barbed suture as claimed in claim 16, further comprising a support element interconnecting at least one of said barbs and said flexible thread for reinforcing said at least one barb and resisting flexure of said at least one barb toward the leading end of said flexible thread.

\* \* \* \* \*